(12) United States Patent
Tamura

(10) Patent No.: US 11,553,972 B2
(45) Date of Patent: Jan. 17, 2023

(54) MEDICAL HOLDING APPARATUS AND MEDICAL OBSERVATION SYSTEM

(71) Applicant: Sony Olympus Medical Solutions Inc., Tokyo (JP)

(72) Inventor: Shigeru Tamura, Chiba (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 357 days.

(21) Appl. No.: 16/746,999

(22) Filed: Jan. 20, 2020

(65) Prior Publication Data
US 2020/0297436 A1 Sep. 24, 2020

(30) Foreign Application Priority Data
Mar. 22, 2019 (JP) .............................. JP2019-055735

(51) Int. Cl.
B25J 9/16 (2006.01)
A61B 34/30 (2016.01)
A61B 90/00 (2016.01)
A61B 90/25 (2016.01)

(52) U.S. Cl.
CPC .............. *A61B 34/30* (2016.02); *A61B 90/25* (2016.02); *A61B 90/361* (2016.02); *B25J 9/1697* (2013.01); *A61B 2034/301* (2016.02)

(58) Field of Classification Search
CPC ... B25J 9/1697; B25J 9/1633; G02B 21/0012; G02B 21/32; A61B 1/00149; A61B 2090/508; A61B 34/30; A61B 90/361; A61B 90/25; A61B 90/50; A61B 2034/301

USPC ........................................... 359/384; 600/476
See application file for complete search history.

(56) References Cited

U.S. PATENT DOCUMENTS

| | | | | |
|---|---|---|---|---|
| 5,122,904 A * | 6/1992 | Fujiwara | ................ | A61B 90/25 206/316.1 |
| 6,398,721 B1 * | 6/2002 | Nakamura | ............. | G02B 7/001 600/102 |
| 9,563,045 B2 * | 2/2017 | Doi | ........................ | A61B 90/20 |
| 9,795,453 B2 * | 10/2017 | Tierney | .................. | A61B 34/37 |
| 2019/0015175 A1 * | 1/2019 | Tamura | .................. | B25J 9/1697 |

FOREIGN PATENT DOCUMENTS

JP 2017-158969 A 9/2017

* cited by examiner

*Primary Examiner* — Dalena Tran
(74) *Attorney, Agent, or Firm* — Xsensus LLP (57) ABSTRACT

A medical holding apparatus includes: a support including a plurality of arms, and a plurality of joints configured to connect the plurality of arms, the support being configured to support an imaging unit at a distal end thereof; a load applying mechanism arranged in at least one of the joints and configured to apply a resistance load against operation of the at least one of the joints to the support; and a processor comprising hardware, the processor being configured to: set torque to be applied by the load applying mechanism based on an operating state of the imaging unit; and apply a load corresponding to the set torque to the load applying mechanism when a rotation inhibit state of each of the arms of the support is released.

9 Claims, 6 Drawing Sheets

MEDICAL HOLDING APPARATUS AND MEDICAL OBSERVATION SYSTEM

This application claims priority from Japanese Application No. 2019-055735, filed on Mar. 22, 2019, the contents of which are incorporated by reference herein in its entirety.

BACKGROUND

The present disclosure relates to a medical holding apparatus and a medical observation system.

In a medical field, a medical observation apparatus including an imaging unit that captures an image of an observation object in an enlarged manner, and a support unit that includes a plurality of arm parts and a plurality of joint parts for connecting the plurality of arm parts and supports the imaging unit at a distal end thereof has been known (for example, see JP 2017-158969 A). In the medical observation apparatus described in JP 2017-158969 A, the imaging unit is moved three-dimensionally by using operation of each of the joint parts, and located at a desired position. Then, the image captured by the imaging unit is displayed on an external display apparatus.

Meanwhile, in the medical observation apparatus that moves the imaging unit three-dimensionally by using operation of each of the joint parts, there is a problem in that an imaging field of view is reduced with an increase in a magnification that is used for observation, and a target region in the observation object disappears (an image is missed) from a screen of the display apparatus only by applying a weak force to the imaging unit (only by slightly moving the imaging unit). To cope with the problem as described above, in the medical observation apparatus described in JP 2017-158969 A, a certain load is applied to each of the joint parts to control movement of each of the joint parts, to thereby prevent missing of an image.

SUMMARY

Meanwhile, in the medical observation apparatus, as one of scenes in which the imaging unit is moved, the imaging unit may be simply evacuated from an observation position, instead of changing the observation position as described above. When the imaging unit is to be evacuated from the observation position, and if loads are applied to the joint parts, an extra burden is imposed on a user to move the imaging unit to an evacuation position. Therefore, there is a demand to ensure operability in accordance with scenes in which the imaging unit is moved.

According to one aspect of the present disclosure, there is provided a medical holding apparatus for holding an imaging unit capable of capturing an image of an observation object in an enlarged manner and configured to output an image signal corresponding to the image, the medical holding apparatus including: a support including: a plurality of arms; and a plurality of joints configured to connect the plurality of arms, the support being configured to support the imaging unit at a distal end thereof; a load applying mechanism arranged in at least one of the joints and configured to apply a resistance load against operation of the at least one of the joints to the support; and a processor comprising hardware, the processor being configured to: set torque to be applied by the load applying mechanism based on an operating state of the imaging unit; and apply a load corresponding to the set torque to the load applying mechanism when a rotation inhibit state of each of the arms of the support is released.

DETAILED DESCRIPTION

Modes for carrying out the present disclosure (hereinafter, referred to as "embodiments") will be described below with reference to the accompanying drawings. The drawings are schematic and different drawings may include a portion that has different dimensional relations or ratios.

Embodiment

Figure 1:
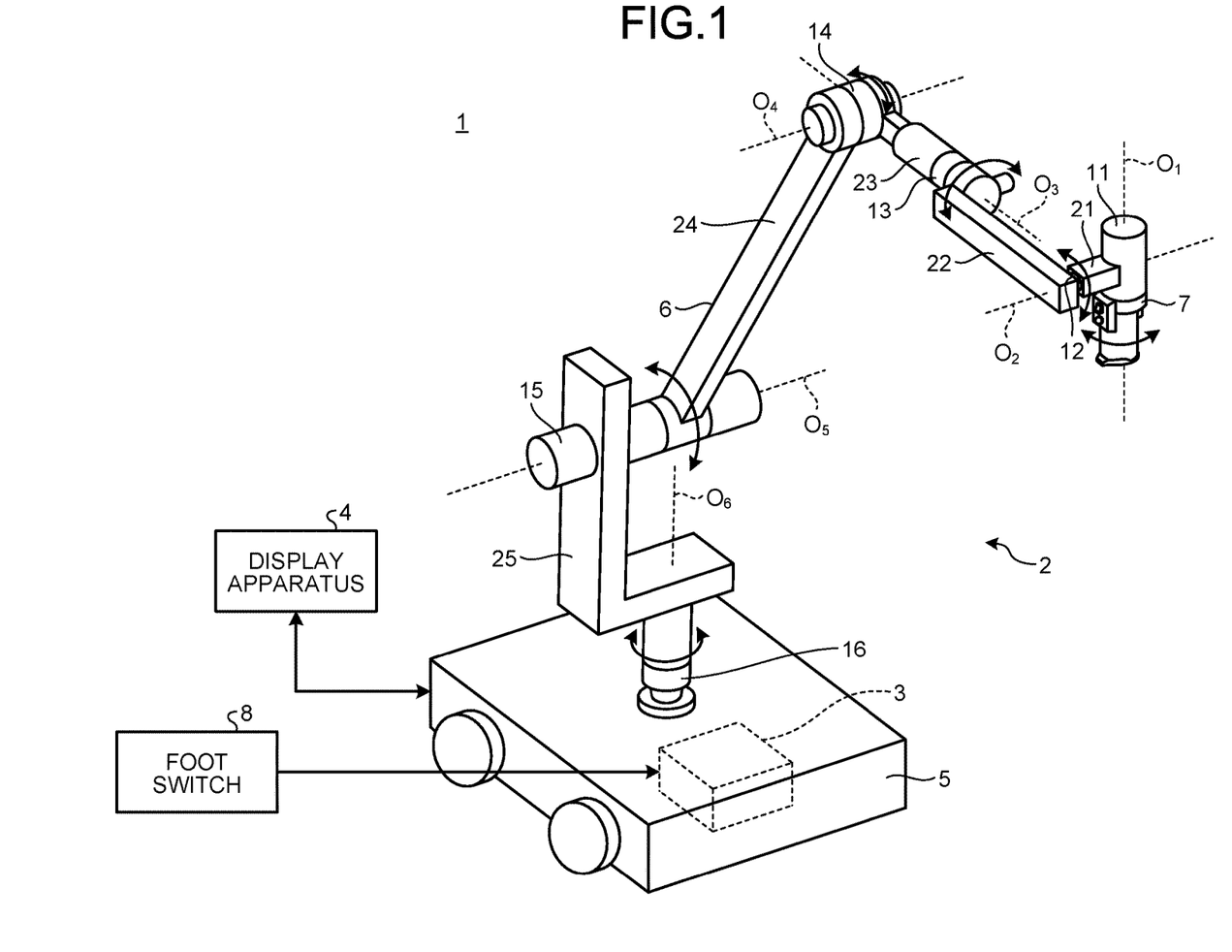
FIG. 1 is a perspective view illustrating an external configuration of a medical observation system according to one embodiment.

FIG. 1 is a diagram illustrating a configuration of a medical observation system according to one embodiment. A medical observation system 1 illustrated in FIG. 1 includes a medical observation apparatus (hereinafter, referred to as an observation apparatus) 2 having a function as a microscope that captures an image of a microstructure of an observed body in an enlarged manner, a control device 3 that is housed in the observation apparatus 2 and integrally controls operation of the medical observation system 1, and a display apparatus 4 that displays an image captured by the observation apparatus 2.

The observation apparatus 2 includes a base part 5 that is movable on a floor surface, a support unit 6 that is supported by the base part 5, and a columnar microscope unit 7 that is disposed at a distal end of the support unit 6 and captures an image of a micro region of an observed body in an enlarged manner. Further, a light source device that supplies illumination light to the observation apparatus 2 via a light guide that is configured with an optical fiber or the like may be connected to the observation apparatus 2.

In the observation apparatus 2, for example, a group of cables including a transmission cable or the like, which includes a signal line (thin coaxial cable) for transmitting signals between the control unit and the microscope unit 7, is arranged from the base part 5 to the microscope unit 7. The group of cables is arranged along the support unit 6. The thin coaxial cable is a cable with a smaller diameter than a diameter of a light guide cable.

The support unit 6 includes a first joint part 11, a first arm part 21, a second joint part 12, a second arm part 22, a third joint part 13, a third arm part 23, a fourth joint part 14, a fourth arm part 24, a fifth joint part 15, a fifth arm part 25, and a sixth joint part 16.

The support unit 6 includes four sets, each including two arm parts and a joint part that connects one (distal end side) of the two arm parts to the other one (proximal end side) of the two arm parts in a rotatable manner. Specifically, the four sets are as follows: (the first arm part 21, the second joint part 12, and the second arm part 22), (the second arm part 22, the third joint part 13, and the third arm part 23), (the third arm part 23, the fourth joint part 14, and the fourth arm part 24), and (the fourth arm part 24, the fifth joint part 15, and the fifth arm part 25).

The first joint part 11 holds the microscope unit 7 on a distal end side in such a manner that the microscope unit 7 may rotate, and is held by the first arm part 21 in such a manner that a proximal end side thereof is fixed to a distal end portion of the first arm part 21. The first joint part 11 has a cylindrical shape and holds the microscope unit 7 such that the microscope unit 7 may rotate about a first axis $O_1$ that is a central axis in a height direction. The first arm part 21 has a shape that extends from a side surface of the first joint part 11 in a direction perpendicular to the first axis $O_1$. A detailed configuration of the first joint part 11 will be described later.

The second joint part 12 holds the first arm part 21 on a distal end side in such a manner that the first arm part 21 may rotate, and is held by the second arm part 22 in such a manner that a proximal end side thereof is fixed to a distal end portion of the second arm part 22. The second joint part 12 has a cylindrical shape and holds the first arm part 21 such that the first arm part 21 may rotate about a second axis $O_2$ that is a central axis in a height direction and that is an axis perpendicular to the first axis $O_1$. The second arm part 22 has an approximately L-shape, and is connected to the second joint part 12 at an end portion of a vertical portion of the L-shape.

The third joint part 13 holds a horizontal portion of the L-shape of the second arm part 22 on a distal end side in such a manner that the second arm part 22 may rotate, and is held by the third arm part 23 in such a manner that a proximal end side thereof is fixed to a distal end portion of the third arm part 23. The third joint part 13 has a cylindrical shape and holds the second arm part 22 such that the second arm part 22 may rotate about a third axis $O_3$ that is a central axis in a height direction, that is an axis perpendicular to the second axis $O_2$, and that is an axis parallel to a direction along which the second arm part 22 extends. A distal end side of the third arm part 23 is formed in a cylinder, and a hole portion is formed on a proximal end side of the third arm part 23 such that the hole portion penetrates in a direction perpendicular to a height direction of the cylinder on the distal end side. The third joint part 13 is held by the fourth joint part 14 via the hole portion in such a manner that the third joint part 13 may rotate.

The fourth joint part 14 holds the third arm part 23 on a distal end side in such a manner that the third arm part 23 may rotate, and is held by the fourth arm part 24 in such a manner that a proximal end side thereof is fixed to the fourth arm part 24. The fourth joint part 14 has a cylindrical shape and holds the third arm part 23 such that the third arm part 23 may rotate about a fourth axis $O_4$ that is a central axis in a height direction and that is an axis perpendicular to the third axis $O_3$.

The fifth joint part 15 holds the fourth arm part 24 on a distal end side in such a manner that the fourth arm part 24 may rotate, and a proximal end side of the fifth joint part 15 is fixedly mounted on the fifth arm part 25. The fifth joint part 15 has a cylindrical shape and holds the fourth arm part 24 such that the fourth arm part 24 may rotate about a fifth axis $O_5$ that is a central axis in a height direction and that is an axis parallel to the fourth axis $O_4$. The fifth arm part 25 includes an L-shaped portion and a bar-shaped portion that extends downward from a horizontal portion of the L-shaped portion. The proximal end side of the fifth joint part 15 is mounted on an end portion of a vertical portion of the L-shaped portion of the fifth arm part 25.

The sixth joint part 16 holds the fifth arm part 25 on a distal end side in such a manner that the fifth arm part 25 may rotate, and a proximal end side of the sixth joint part 16 is fixedly mounted on an upper surface of the base part 5. The sixth joint part 16 has a cylindrical shape and holds the fifth arm part 25 such that the fifth arm part 25 may rotate about a sixth axis $O_6$ that is a central axis in a height direction and that is an axis perpendicular to the fifth axis $O_5$. A proximal end portion of the bar-shaped portion of the fifth arm part 25 is mounted on a distal end side of the sixth joint part 16.

The support unit 6 configured as described above realizes movement with a total of six kinds of flexibility, such as three kinds of translational flexibility and three kinds of rotational flexibility, in the microscope unit 7.

The first joint part 11 to the sixth joint part 16 include electromagnetic brakes that inhibit rotation of the microscope unit 7 and the first arm part 21 to the fifth arm part 25, and torque generation units (load applying mechanisms) that generate loads (torque) to be applied when the microscope unit 7, the first arm part 21, and the second arm part 22 rotate.

Each of the electromagnetic brakes is released when an arm operation switch 73 (to be described later) arranged in the microscope unit 7 is pressed, and allows the microscope unit 7 and the first arm part 21 to the fifth arm part 25 to rotate. It may be possible to adopt air brakes instead of the electromagnetic brakes. The electromagnetic brakes correspond to a rotation inhibiting means.

The torque generation unit will be described later.

Further, an encoder and an actuator may be mounted on at least the second joint part 12 and the third joint part 13 (the second axis $O_2$ and the third axis $O_3$) among the joint parts, in addition to the electromagnetic brakes as described above. For example, if an encoder is mounted on the first joint part 11, the encoder detects a rotation angle with respect to the first axis $O_1$. The actuator is configured with, for example, an electric motor, such as a servomotor, is driven under the control of the control device 3 based on pressing of a foot switch 8 to be described later, and causes rotation by a predetermined angle to occur at the joint part. A rotation angle at the joint part is set by the control device 3, as a value that is needed to move the microscope unit 7 in accordance with a pressing mode of the foot switch 8, based on a rotation angle with respect to each of the rotation axes (the first axis $O_1$ to the sixth axis $O_6$). In this manner, the joint part in which an active driving mechanism, such as an actuator, is arranged constitutes a rotation axis that actively rotates when drive of the actuator is controlled. The actuator corresponds to a driving means that drives the support unit.

Figure 2:
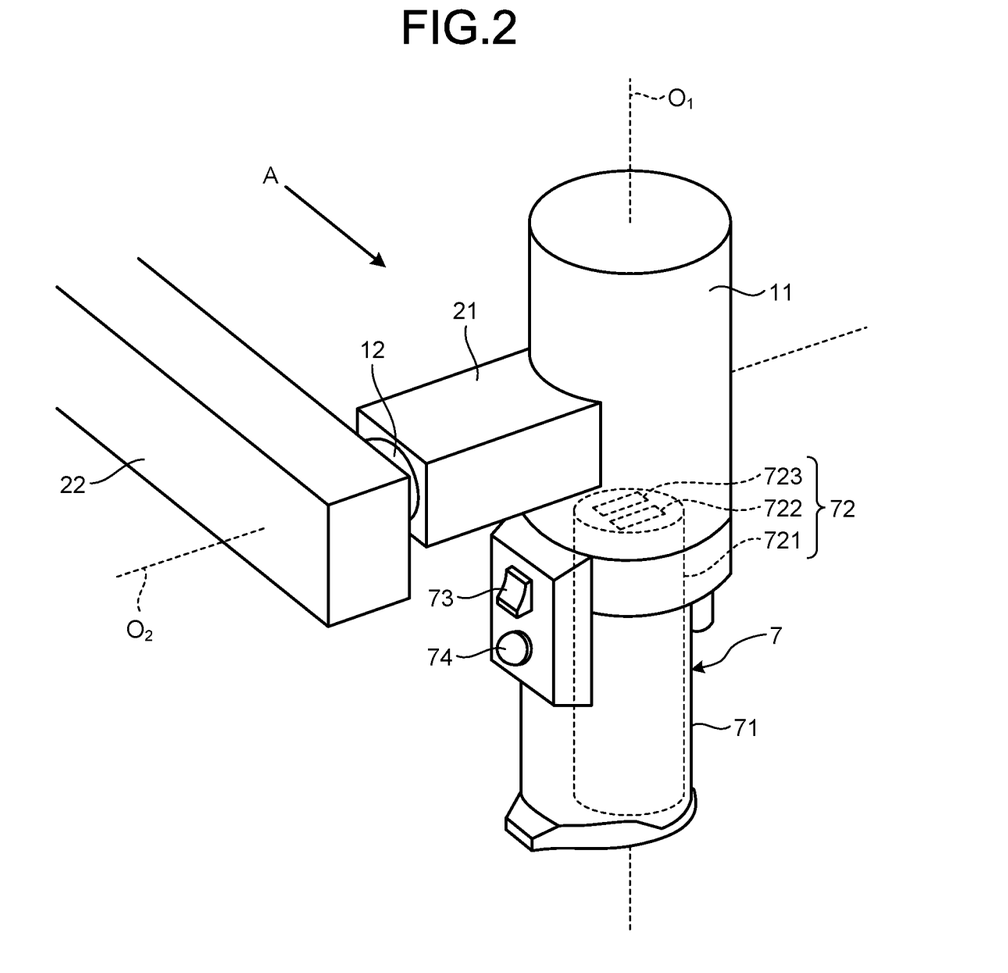
FIG. 2 is an enlarged perspective view illustrating configurations of a microscope unit and peripheral units of the microscope unit in the medical observation apparatus according to the embodiment.
Figure 3:
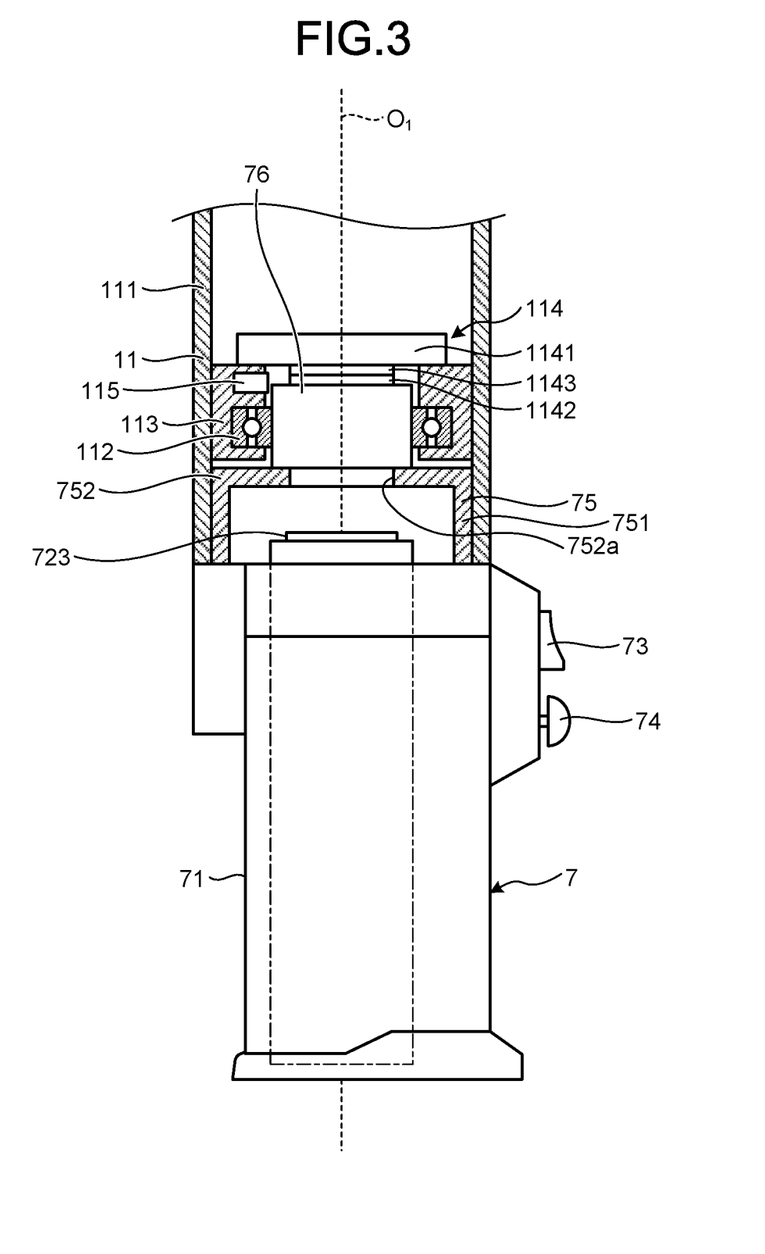
FIG. 3 is a partial cross-sectional view, viewed from a direction of an arrow A in FIG. 2.

FIG. 2 is an enlarged perspective view illustrating configurations of the microscope unit 7 and peripheral units of the microscope unit 7 in the observation apparatus 2. FIG. 3 is a partial cross-sectional view, viewed from a direction of an arrow A in FIG. 2. The configuration of the microscope unit 7 will be described below with reference to FIG. 2 and FIG. 3.

The microscope unit 7 includes a tubular part 71 having a cylindrical shape, an imaging unit 72 that is arranged in a hollow part of the tubular part 71 and captures an image of an observed body in an enlarged manner, the arm operation switch 73 that releases the electromagnetic brakes of the first joint part 11 to the sixth joint part 16 and receives input of operation for allowing each of the joint parts to rotate, a cross lever 74 capable of changing an enlargement magnification and a focal length to the observed body in the imaging unit 72, an upper cover 75 that is formed on an upper circumference of the imaging unit 72 and fitted into the first joint part 11, and a hollow cylindrical shaft part 76 that extends from the upper cover 75 along the first axis $O_1$.

The tubular part 71 is formed in a cylindrical shape with a smaller diameter than a diameter of the first joint part 11, and a cover glass (not illustrated) for protecting the imaging unit 72 is arranged on an opening surface of a lower end portion of the tubular part 71. The tubular part 71 need not always be formed in a cylindrical shape, but may be formed in a tubular shape whose cross section perpendicular to the height direction has an elliptical or polygonal shape.

The imaging unit 72 includes an optical system 721 that has a plurality of lenses arranged such that optical axes match the first axis $O_1$, that condenses light from the observed body, and that forms an image, and two imaging elements 722 and 723 that receive the light condensed by the optical system 721, perform photoelectric conversion on the light, and generate imaging signals. In FIG. 2, only a tubular casing that houses the plurality of lenses of the optical system 721 is illustrated.

The optical system 721 is able to change an enlargement magnification of an image of the observed body and a focal length to the observed body in accordance with operation on the cross lever 74.

Each of the imaging elements 722 and 723 is configured using a charge coupled device (CCD) or a complementary metal oxide semiconductor (CMOS). The imaging elements 722 and 723 generate two imaging signals with disparities, as imaging signals for generating a three-dimensional image. The imaging signals are output, as digital signals, from the imaging elements 722 and 723.

The arm operation switch 73 is a push-button switch. While a user is pressing the arm operation switch 73, the electromagnetic brakes of the first joint part 11 to the sixth joint part 16 are released. The arm operation switch 73 is arranged on a side surface opposite to a side surface that faces the user when the user operates the microscope unit 7, in other words, on the side surface that is located in the user's blind spot during operation of the microscope unit 7. The arm operation switch 73 constitutes a part of an operation input unit that receives input of operation on the observation apparatus 2.

The cross lever 74 may be operated in a height direction of the tubular part 71 and a circumferential direction perpendicular to the height direction. The cross lever 74 is arranged on a side surface of the tubular part 71 so as to be located below the arm operation switch 73 on the side surface along the height direction of the tubular part 71. The cross lever 74 also constitutes a part of the operation input unit that receives input of operation on the observation apparatus 2, similarly to the arm operation switch 73.

If the cross lever 74 is operated along the height direction of the tubular part 71 from the position as illustrated in FIG. 2, the enlargement magnification is changed, and, if the cross lever 74 is operated along the circumferential direction of the tubular part 71 from the position as illustrated in FIG. 2, a focal length to the observed body is changed. For example, if the cross lever 74 is moved upward along the height direction of the tubular part 71, the enlargement magnification increases, and if the cross lever 74 is moved downward along the height direction of the tubular part 71, the enlargement magnification decreases. Further, if the cross lever 74 is moved clockwise along the circumferential direction of the tubular part 71, the focal length to the observed body increases, and if the cross lever 74 is moved counterclockwise along the circumferential direction of the tubular part 71, the focal length to the observed body decreases. The moving directions and assignment of operation of the cross lever 74 are not limited to those as described above.

The upper cover 75 includes a cylindrical part 751 and a hollow disk part 752 that is arranged on an upper end portion of the cylindrical part 751 and that has the same diameter as that of the cylindrical part 751. The cylindrical shaft part 76 that extends along the first axis $O_1$ and that has a hollow part communicating with a hollow part 752a of the hollow disk part 752 is mounted on the hollow disk part 752. A coaxial wire connecting to the imaging unit 72 and a light guide that guides illumination light emitted from a distal end of the microscope unit 7 are inserted in the hollow part 752a and the hollow part of the shaft part 76.

Configurations of main parts of the first joint part 11 will be described below with reference to FIG. 3. The first joint part 11 includes an outer frame 111 which has an upper end portion formed in a bottomed cylindrical shape and in which the upper cover 75 of the microscope unit 7 is fitted along an inner periphery, a shaft support part 112 that supports the shaft part 76 of the microscope unit 7 in such a manner that the shaft part 76 may rotate, a holder part 113 that is fixed to the outer frame 111 and that fixedly holds an outer periphery of the shaft support part 112, a torque generation unit 114 that adjusts a load with respect to rotation of the shaft part 76, and a detection unit 115 that detects a moving speed of the microscope unit 7. The outer frame 111 is fixedly connected to the first arm part 21. A through hole (not illustrated) is formed in a portion connected to the first arm part 21 on the outer frame 111. The through hole communicates with the inside of the first arm part 21. Meanwhile, in FIG. 3, illustration of configurations of the electromagnetic brakes and the actuators are omitted.

In the first joint part 11, the outer frame 111 and the holder part 113 correspond to a fixing part, and the shaft part 76 corresponds to a movable part.

In the observation apparatus 2, the user is able to press the arm operation switch 73 and operate the support unit 6 while naturally holding the microscope unit 7. In particular, because the arm operation switch 73 is arranged on the side surface that is located in the user's blind spot among the side surfaces of the microscope unit 7 (the side surface opposite to the side surface that faces the user), the user is able to perform operation of continuously pressing the arm operation switch 73 and operation of pressing and releasing the arm operation switch 73 without feeling uncomfortable even when the user rotates or inclines the microscope unit 7 while holding the microscope unit 7 in the user's hand.

Further, in the observation apparatus 2, it is not necessary to separately arrange a grip portion equipped with the arm operation switch 73, so that it is possible to configure the microscope unit 7 with a small size and it is possible to adequately ensure the user's field of vision.

Furthermore, in the observation apparatus 2, the user is allowed to hold the periphery of the microscope unit 7 in the user's hand, and therefore, the user is able to intuitively recognize a position of the optical axis of the optical system 721, in other words, a direction of the imaging field of view, and is able to easily move the microscope unit 7 to a desired position; thus, the operability is excellent.

Configurations of the torque generation unit 114 and the detection unit 115 arranged in the first joint part 11 will be described below with reference to FIG. 3. As one example, the configuration of the torque generation unit 114 arranged in the first joint part 11 will be described using the configuration as illustrated in FIG. 3; however, the same torque generation unit 114 is also arranged in the second joint part 12 and the third joint part 13.

The torque generation unit 114 applies a load corresponding to set torque to the shaft part 76 that rotates about the first axis $O_1$. The torque generation unit 114 is configured using, for example, a magnetic fluid (MR fluid).

The MR fluid device includes a fixed disk 1141 that is fixed to the holder part 113, a movable disk 1142 that is fixed to the shaft part 76 and is rotatable in synchronization with rotation of the shaft part 76, in this example, rotatable around the first axis $O_1$, and a fluid container 1143 that is arranged between the fixed disk 1141 and the movable disk 1142 and that contains magnetic fluid. Further, magnets with opposite magnetic poles are arranged in the fixed disk 1141 and the movable disk 1142. Meanwhile, the fluid container 1143 also contains fluid that causes the magnetic fluid to float.

In the MR fluid device, a chain cluster is formed when a magnetic field is applied to the magnetic fluid. The chain cluster connects the fixed disk 1141 and the movable disk 1142 and generates a shear stress at the time of rotation of the movable disk 1142. The shear stress acts as a resisting force at the time of rotation of the movable disk 1142. In other words, the shear stress generated by the chain cluster acts as a break force of the movable disk 1142.

By changing the magnitude of the magnetic field applied to the magnetic fluid, the size and the number of the chain clusters are changed, and the shear stress increases with an increase in the magnetic field. With use of this, it is possible to adjust the magnitude of the torque that is applied with respect to the rotation of the shaft part 76.

Meanwhile, the torque generation unit 114 may be configured by using a brushless DC motor, an electromagnetic brake (spring type or a permanent type), an electromagnetic clutch, or the like, instead of the MR fluid device.

The detection unit 115 detects the moving speed of the imaging unit 72. The detection unit 115 is configured using a well-known displacement detector or a well-known velocity detector, such as an encoder or an acceleration sensor. The detection unit 115 outputs a detection result to the control device 3.

Figure 4:
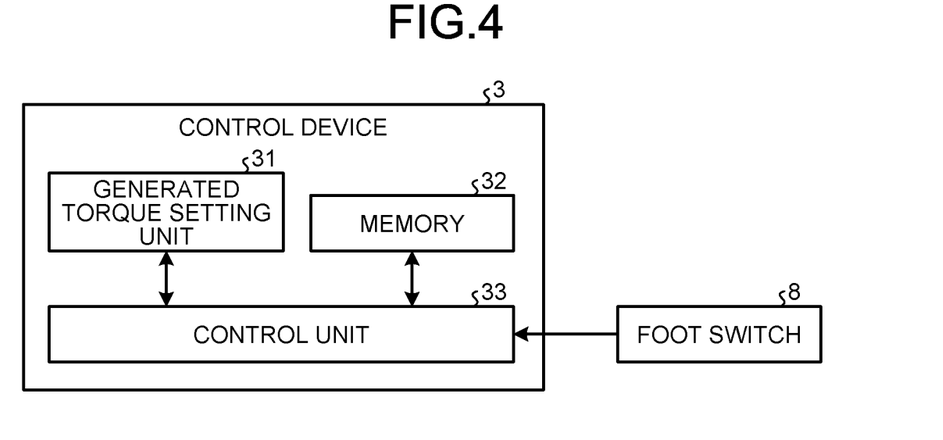
FIG. 4 is a block diagram illustrating a configuration of a control device included in the medical observation apparatus according to the embodiment.

Explanation of the configuration of the medical observation system 1 is continued below. FIG. 4 is a block diagram illustrating a configuration of the control device included in the medical observation apparatus according to the embodiment.

The control device 3 is incorporated in the base part 5 (see FIG. 1), receives an imaging signal output by the observation apparatus 2, generates three-dimensional image data to be displayed by performing predetermined signal processing on the imaging signal, and controls rotation of the arm parts. The control device 3 includes a generated torque setting unit 31, a memory 32, and a control unit 33.

Further, the foot switch 8 that is a part operated with a user's foot and that inputs a signal corresponding to pressing performed by the user is connected to the control device 3. The foot switch 8 may be inclined in a plurality of directions, and moving directions of the microscope unit 7 (the imaging field of view) are assigned to inclination directions. It may be possible to change a driving speed (for example, the moving speed of the microscope unit 7) in accordance with an inclination angle.

When the arm operation switch 73 is pressed, the generated torque setting unit 31 acquires a detection result from the detection unit 115, acquires a zoom magnification (enlargement factor), working distance (WD), and the moving speed of the microscope unit 7 at the time of pressing the switch, and sets torque to be generated in the first joint part 11 to the third joint part 13.

The memory 32 is realized using a semiconductor memory, such as a flash memory, a dynamic random access memory (DRAM), or a read only memory (ROM), and records therein communication information data (for example, communication format information or the like), data related to assignment of the inclination directions of the foot switch 8 and the rotation directions of the joint parts, and data related to torque setting to be described later. The memory 32 may record therein various programs or the like to be executed by the control device 3.

The control unit 33 controls each of the units of the medical observation system 1. Specifically, for example, the control unit 33 turns on and off the electromagnetic brake of each of the joint parts in accordance with operation of pressing and releasing the arm operation switch 73, drives the actuators in accordance with operation of pressing and releasing the foot switch 8 to thereby rotate the joint parts, controls an imaging process performed by the imaging unit 72, and performing image processing on a signal captured by the imaging unit 72. The control unit 33 turns off the actuators of the joint parts while the foot switch 8 is not pressed, and turns on the actuators of the joint parts while the foot switch 8 is pressed so as to rotate the joint parts in accordance with the inclination direction of the foot switch 8 and change the position of the microscope unit 7. For example, if the actuators are arranged in the second joint part 12 (the second axis $O_2$) and the third joint part 13 (the third axis $O_3$), it is possible to move the imaging field of view in two directions perpendicular to each other on an imaging plane (focal point plane) in response to pressing of the foot switch.

The generated torque setting unit 31 and the control unit 33 are configured using a general-purpose processor, such as a central processing unit (CPU), including an internal memory (not illustrated) in which a program is recorded, or a dedicated processor, for example, various arithmetic circuits, such as an application specific integrated circuit (ASIC), that implement specific functions. Further, the generated torque setting unit 31 and the control unit 33 may be configured using a field programmable gate array (FPGA) (not illustrated) that is one of a programmable integrated circuit. If the generated torque setting unit 31 and the control unit 33 are configured using an FPGA, it may be possible to provide a memory for storing configuration data, and configure the FPGA that is a programmable integrated circuit by using the configuration data read from the memory.

The display apparatus 4 receives, from the control device 3, three-dimensional image data generated by the control device 3, and displays a three-dimensional image corresponding to the three-dimensional image data. The display apparatus 4 as described above includes a display panel made with liquid crystal or organic electro luminescence (EL).

An outline of surgery that is performed using the medical observation system 1 configured as described above will be described below. A surgeon wears glasses for a three-dimensional image, views the three-dimensional image displayed by the display apparatus 4, grips and moves the microscope unit 7 to a desired position while pressing the arm operation switch 73 of the microscope unit 7, determines an imaging field of view of the microscope unit 7, and releases his/her finger from the arm operation switch 73. Accordingly, the electromagnetic brakes of the first joint part 11 to the sixth joint part 16 operate, and the imaging field of view of the microscope unit 7 is fixed. Thereafter, the surgeon adjusts an enlargement magnification and a focal length to an observed body. The display apparatus 4 displays the three-dimensional image, and therefore the surgeon is able to recognize a surgery site three-dimensionally via the three-dimensional image.

In the embodiment, a medical holding apparatus is configured by using at least the support unit 6, the generated torque setting unit 31, the control unit 33, and the torque generation unit (the torque generation unit 114).

Figure 5:
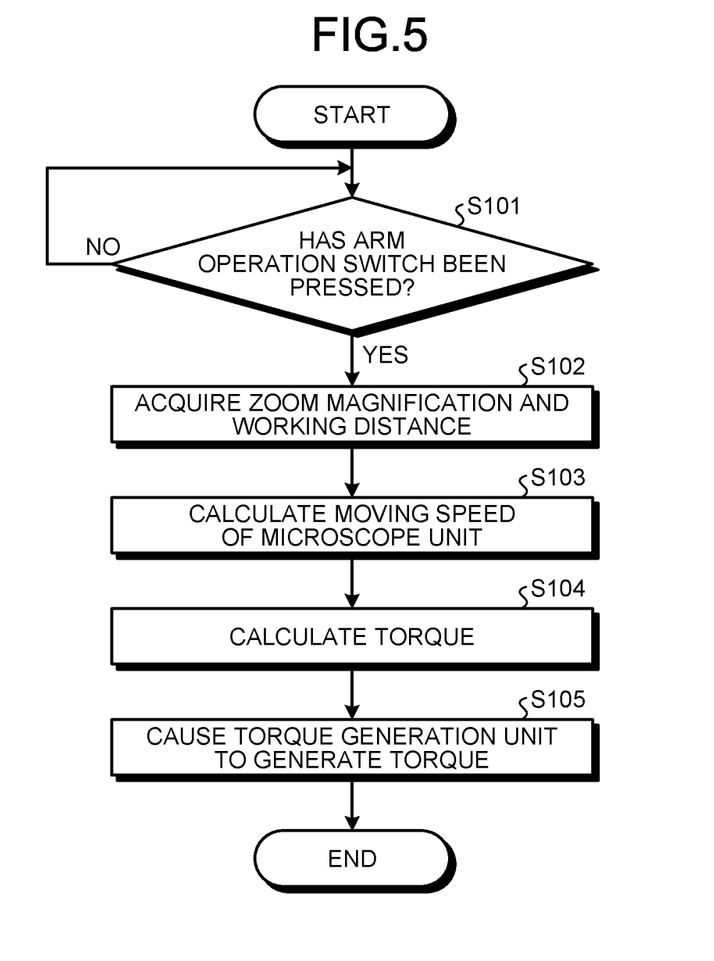
FIG. 5 is a flowchart illustrating a torque setting process performed by the medical observation system according to the embodiment.

A torque setting process performed by the medical observation system 1 will be described below with reference to FIG. 5. FIG. 5 is a flowchart illustrating the torque setting process performed by the medical observation system according to the embodiment.

In the torque setting process, the control unit 33 determines whether the arm operation switch 73 has been pressed (Step S101). If the control unit 33 determines that the arm operation switch 73 has not been pressed (Step S101: No), the control unit 33 repeats the process of determining the pressing. In contrast, if the control unit 33 determines that the arm operation switch 73 has been pressed (Step S101: Yes), the process proceeds to Step S102. In this manner, in the torque setting process, if the arm operation switch 73 is pressed and rotation inhibit states of the microscope unit 7 and the first arm part 21 to the fifth arm part 25 are released, the torque setting process is started.

At Step S102, the control unit 33 acquires a zoom magnification and a working distance at the time of pressing the arm operation switch 73. The zoom magnification is calculated based on, for example, a lens position. The working distance is calculated based on, for example, a detection value that is detected by an encoder arranged in the imaging unit 72. The control unit 33 may extract and acquire the zoom magnification and the working distance from, for example, current setting information on the microscope unit 7 (the imaging unit 72) that is stored in the memory 32.

At Step S103 following Step S102, the generated torque setting unit 31 calculates the moving speed of the microscope unit 7. The generated torque setting unit 31 acquires a detection result from the detection unit 115 and calculates the moving speed of the microscope unit 7. Specifically, if the detection unit 115 is an encoder for example, the generated torque setting unit 31 converts a displacement amount of the microscope unit 7 to an electrical signal, processes the converted signal, and calculates the moving speed.

At Step S104 following Step S103, the generated torque setting unit 31 calculates torque to be generated by the torque generation unit 114, by using the zoom magnification, the working distance, and the moving speed that are acquired as above.

Here, the generated torque setting unit 31 sets torque based on a magnitude relationship between each of parameters and generated torque as illustrated in Table 1 below. For example, if the working distance is long or the zoom magnification is high, the field of view is largely changed only by slightly moving the microscope unit 7, and therefore, the generated torque is increased to prevent movement. Further, if the moving speed of the microscope unit 7 is high, it is assumed that the position of the microscope unit 7 is to be largely moved to evacuate the microscope unit 7 from an observation position, and therefore, the generated torque is reduced to reduce a load related to movement of the microscope unit 7.

TABLE 1

|  | Generated torque | |
| --- | --- | --- |
|  | Large | Small |
| WD | Long | Short |
| Zoom magnification | High | Low |
| Moving speed | Fast | Slow |

Meanwhile, low and high of the zoom magnification are determined based on low and high with respect to a reference magnification that is set in advance.

Specifically, the generated torque setting unit 31 calculates torque by using Equation (1) below, where $T_{TTL}$ represents torque, $T_{ZOOM}$ represents a parameter calculated from the zoom magnification, $T_{WD}$ represents a parameter calculated from the working distance, and $T_V$ represents a parameter calculated from the moving speed. For example, each of the parameters has a proportional relationship to each of acquired values.

$$T_{TTL} = T_{ZOOM} + T_{WD} - T_V \qquad (1)$$

Meanwhile, Equation (1) may be shared among the first joint part 11 to the third joint part 13, or it may be possible to set equations for which different coefficients are set for respective joint parts and from which different calculation results are obtained. If the calculation results are different, torque of the third joint part 13 may be the largest and torque of the first joint part 11 may be the smallest, for example.

At Step S105 following Step S104, the control unit 33 causes the torque generation unit (the torque generation unit 114) of each of the joint parts to generate the torque calculated by the generated torque setting unit 31. At this time, it may be possible to generate a click feeling by inputting a rectangular pulse in the torque generation unit so that the user may feel a change of a load in operation of the microscope unit 7.

The torque generation unit generates the chain cluster as described above, and the chain cluster applies the brake force to the joint parts. By setting the torque using the zoom magnification, the working distance, and the moving speed, a small brake force is applied when the microscope unit 7 is evacuated and a large break force is applied during observation, for example.

In the embodiment as described above, a load (torque) applied to the joint parts is set by using the zoom magnification, the working distance, and the moving speed, so that it is possible to apply a load with appropriate torque in accordance with a user's moving scene of the microscope unit 7. According to the embodiment, it is possible to improve operability for movement of the imaging unit 72 (the microscope unit 7).

Further, in the configuration in which a certain load is applied to the joint parts as in the related art, electric power for continuously applying the certain load is consumed; however, in the embodiment, the load is adjusted in accordance with the moving scene, so that it is possible to reduce consumption of electric power by applying a load with low electric power if a large load is not needed.

In the embodiment, even when the arm operation switch 73 is not pressed and when the electromagnetic brakes are operating, the torque generation unit may apply a load corresponding to the torque set by the generated torque setting unit 31 to the shaft part 76.

First Modification

A first modification of the above-described embodiment will be described below with reference to FIG. 6. A configuration of a medical observation system according to the first modification is the same as that of the above-described embodiment, and therefore, explanation thereof will be omitted. In the first modification, a torque setting process is different from that of the embodiment. In the following, the torque setting process according to the first modification will be described.

Figure 6:
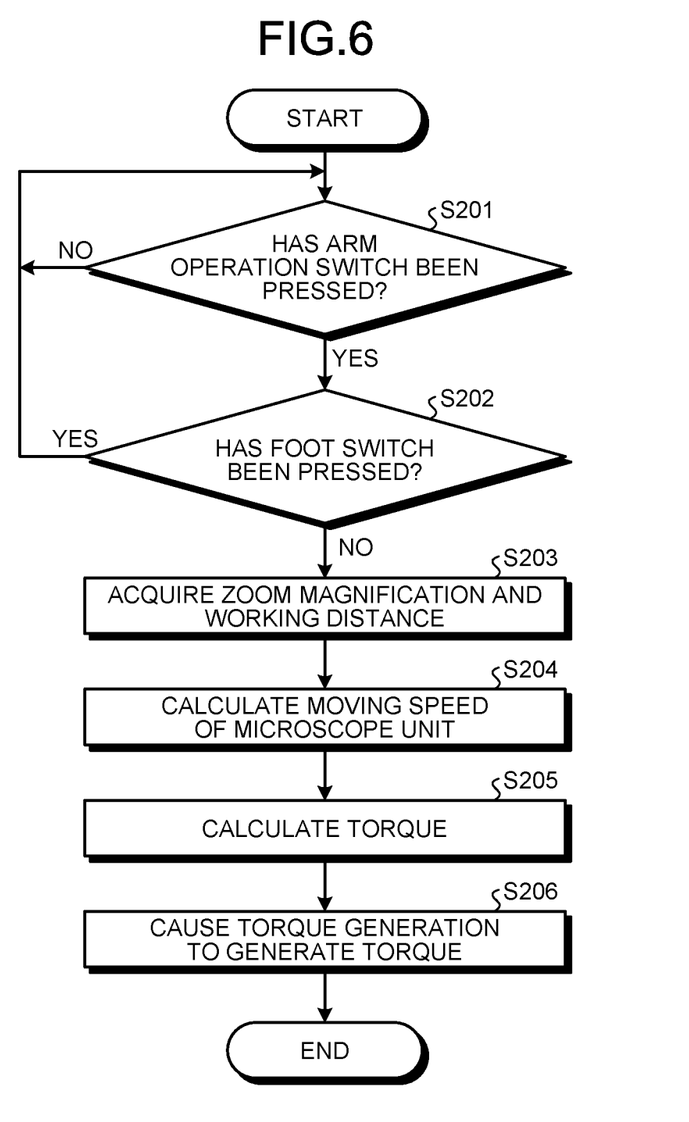
FIG. 6 is a flowchart illustrating a torque setting process performed by a medical observation system according to a first modification of the embodiment.

FIG. 6 is a flowchart illustrating the torque setting process performed by the medical observation system according to the first modification of the embodiment.

In the torque setting process, the control unit 33 determines whether the arm operation switch 73 has been pressed (Step S201). If the control unit 33 determines that the arm operation switch 73 has not been pressed (Step S201: No), the control unit 33 repeats the process of determining the pressing. In contrast, if the control unit 33 determines that the arm operation switch 73 has been pressed (Step S201: Yes), the process proceeds to Step S202.

At Step S202, the control unit 33 determines whether the foot switch 8 has been pressed. If the control unit 33 determines that the foot switch 8 has been pressed (Step S202: Yes), the process returns to Step S201. In contrast, if the control unit 33 determines that the foot switch 8 has not been pressed (Step S202: No), the process proceeds to Step S203.

In the torque setting process according to the first modification, the torque setting process is started if the arm operation switch 73 is pressed and the rotation inhibit states of the microscope unit 7 and the first arm part 21 to the fifth arm part 25 are released, and if the foot switch 8 is not pressed and the actuators are not driven.

At Step S203, the control unit 33 acquires the zoom magnification and the working distance at the time of pressing the arm operation switch 73, similarly to Step S102.

At Step S204 following Step S203, the generated torque setting unit 31 calculates the moving speed of the microscope unit 7, similarly to Step S103.

At Step S205 following Step S204, the generated torque setting unit 31 calculates torque to be generated by the torque generation unit 114, by using the zoom magnification, the working distance, and the moving speed that are acquired as above, similarly to Step S104.

At Step S206 following Step S205, the control unit 33 causes the torque generation unit (the torque generation unit 114) of each of the joint parts to generate the torque calculated by the generated torque setting unit 31, similarly to Step S105. The torque generation unit generates the chain cluster as described above, and the chain cluster applies the brake force to the joint parts.

In the first modification as described above, when the electromagnetic brakes are released and the actuators of the joint parts are turned off, a load (torque) to be applied to the joint parts is set by using the zoom magnification, the working distance, and the moving speed; therefore, it is possible to apply a load with appropriate torque in accordance with a user's moving scene of the microscope unit 7. Even in the first modification, similarly to the embodiment, it is possible to improve the operability for movement of the imaging unit 72 (the microscope unit 7).

Second Modification

Figure 7:
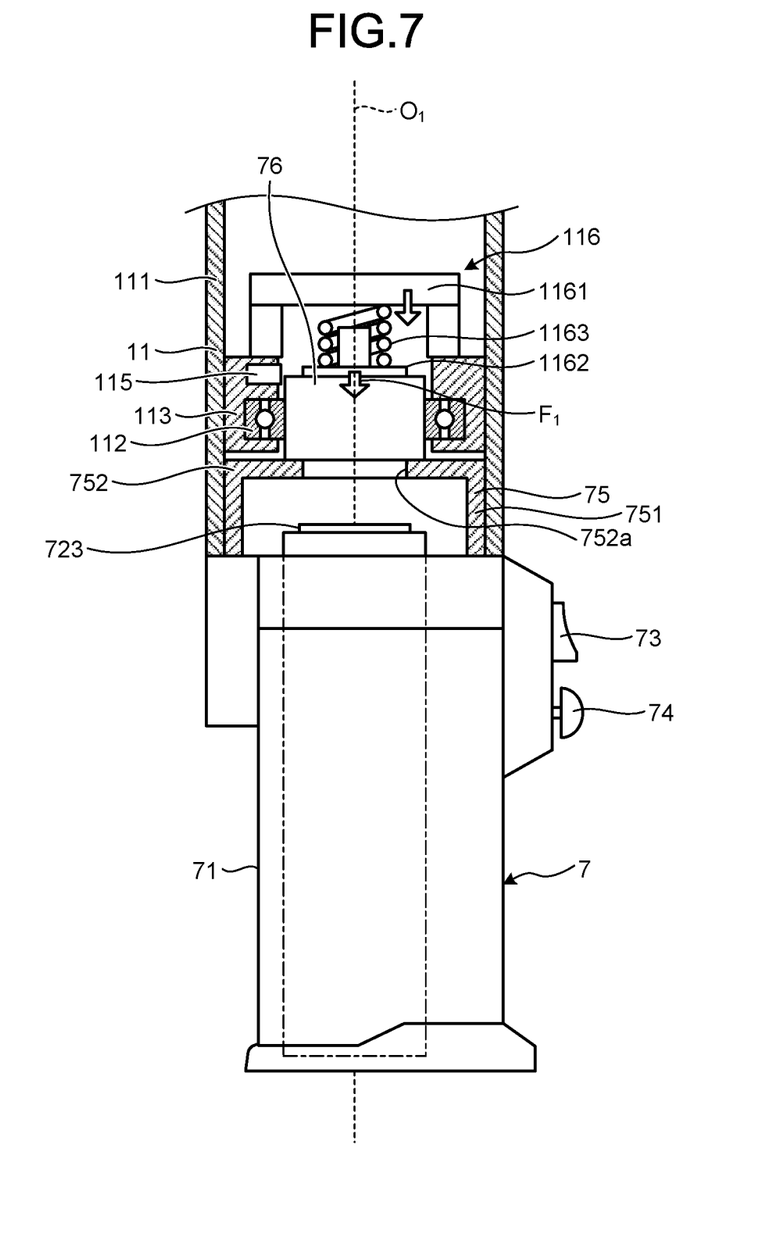
FIG. 7 is a partial cross-sectional view illustrating configurations of a microscope unit and peripheral units of the microscope unit in a medical observation apparatus according to a second modification of the embodiment.

A second modification of the above-described embodiment will be described below with reference to FIG. 7. FIG. 7 is a partial cross-sectional view illustrating configurations of a microscope unit and peripheral units of the microscope unit in a medical observation apparatus according to the second modification of the embodiment. A medical observation system according to the second modification has the same configuration as that of the above-described embodiment except for a configuration of a torque generation unit, and therefore, explanation of the configurations other than the torque generation unit will be omitted. In the second modification, a torque generation unit 116 arranged in the first joint part 11 will be described, but the same torque generation unit may be arranged in the second joint part 12 and the third joint part 13.

The torque generation unit 116 applies a load corresponding to set torque to the shaft part 76 that rotates about the first axis $O_1$. The torque generation unit 116 includes a torque adjustment unit 1161 that is arranged on the holder part 113 and adjusts torque, a pressing unit 1162 that presses the shaft part 76, and a coil spring 1163 that is arranged between the torque adjustment unit 1161 and the pressing unit 1162.

The torque generation unit 116 adjusts a distance between the torque adjustment unit 1161 and the pressing unit 1162 in accordance with torque set by the generated torque setting unit 31. In other words, a pressing amount of the torque adjustment unit 1161 toward the pressing unit 1162 side is adjusted in accordance with the set torque. In this case, the coil spring 1163 is arranged between the torque adjustment unit 1161 and the pressing unit 1162, and a load applied to the pressing unit 1162 is changed depending on the pressing amount. Specifically, with an increase in the pressing amount, in other words, with a decrease in the distance between the torque adjustment unit 1161 and the pressing unit 1162, a load applied to the pressing unit 1162 by the coil spring 1163 is relatively increased. Accordingly, a load $F_1$ that is applied by the pressing unit 1162 to press the shaft part 76 increases, and a resistance force against rotation of the shaft part 76 increases. In contrast, with a decrease in the pressing amount, in other words, with an increase in the distance between the torque adjustment unit 1161 and the pressing unit 1162, the load $F_1$ applied to the pressing unit 1162 by the coil spring 1163 is relatively decreased. Accordingly, the load applied by the pressing unit 1162 to press the shaft part 76 increases, and torque applied to the shaft part 76 decreases.

Meanwhile, the pressing amount with respect to the torque is determined based on a spring constant of the coil spring.

As described above, by adjusting the pressing amount of the torque adjustment unit 1161 in accordance with the set torque, it is possible to adjust a resistance load against rotation of the shaft part 76. Even in the modification, the load (torque) applied to the joint part is set by using the zoom magnification, the working distance, and the moving speed, and the load is applied with appropriate torque in accordance with a user's moving scene of the microscope unit 7.

While the embodiments have been explained above, the present disclosure is not limited to the above described embodiments. For example, it is sufficient that the support unit 6 includes at least a single set of two arm parts and a joint part that connects one of the two arm parts to the other one of the two arm parts in a rotatable manner.

While the example in which the torque is calculated using Equation (1) has been described in the embodiment as described above, it may be possible to input the zoom magnification, the working distance, and the moving speed and determine torque using a table that outputs torque corresponding to the input values.

Further, in the above-described embodiment, it may be possible to detect angles of the first joint part 11 to the sixth joint part 16, detect a moving direction of the microscope unit 7 based on postures of the joint parts, multiply Equation (1) by a coefficient corresponding to a displacement amount in the moving direction (for example, an angle in the moving direction with respect to the first axis $O_1$), and calculate torque in which the postures and the moving direction of the microscope unit 7 are reflected.

Furthermore, in the above-described embodiment, the example has been described in which the torque generation units are arranged on the first joint part 11 to the third joint part 13, but it is sufficient to arrange the torque generation unit on at least one joint part. For example, the torque generation unit may be arranged in only the second joint part 12, arranged in only the second joint part 12 and the third joint part 13, or arranged in the first joint part 11 to the sixth joint part 16.

Moreover, in the above-described embodiment, the example has been described in which the electromagnetic brakes and the torque generation units are arranged in the joint parts, but it may be possible not to arrange the electromagnetic brakes but to fix the joint parts using the torque generation units.

Furthermore, in the above-described embodiment, the example has been described in which the control device 3 is incorporated in the base part 5, but it may be possible to arrange the control device 3 separately from the observation apparatus 2.

Moreover, in the above-described embodiment, the example has been described in which the support unit 6 holds the microscope unit 7, but the support unit 6 may hold a member that is able to perform imaging, instead of the microscope unit 7. For example, the support unit 6 may hold a rigid endoscope at a distal end thereof, or may hold a distal end of a flexible endoscope. If the support unit 6 holds the endoscope, the base part 5 and the support unit 6 function as an endoscope holder.

Furthermore, the imaging unit 72 may include a single imaging element or three or more imaging elements. If the imaging unit 72 includes a single imaging element, the display apparatus 4 displays a two-dimensional image.

Moreover, the operation input unit arranged on the tubular part 71 is not limited to that as described above. For example, it may be possible to separately arrange an operating unit for changing an enlargement magnification and an operating unit for changing a focal length to an observed body.

Furthermore, in the embodiment, the example has been described in which the actuators arranged in the joint parts are driven by the foot switch 8, but embodiments are not limited to this example. It may be possible to perform operation using a switch operated by using other than a foot, such as a switch to be pressed by hand.

Moreover, the medical observation apparatus may be hang on a ceiling of an installation site.

In this manner, the present disclosure may include various embodiments and the like within the scope of the technical ideas specified by the scope of the claims.

As described above, the medical holding apparatus and the medical observation system according to the present disclosure is useful for improving operability for movement of the imaging unit.

According to the present disclosure, it is possible to improve operability for movement of the imaging unit.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical holding apparatus for holding an imager capable of capturing an image of an observation object in an enlarged manner and outputting an image signal corresponding to the image, the medical holding apparatus comprising:
   a support including:
      a plurality of arms; and
      a plurality of joints to connect the plurality of arms, the support being configured to support the imager at a distal end thereof;
   a load applier arranged in at least one of the joints to apply a resistance load against operation of the at least one of the joints to the support; and
   a processor comprising hardware, the processor being configured to:
      set torque to be applied by the load applier based on an operating state of the imager; and
      apply a load corresponding to the set torque to the load applier when a rotation inhibit state of each of the arms of the support is released,
   wherein the processor is configured to set the torque based on an enlargement factor, a working distance, and a moving speed of the imager.

2. The medical holding apparatus according to claim 1, further comprising:
   a driver to drive the support, wherein
   the processor is configured to apply a load corresponding to the set torque to the load applier when the rotation inhibit state of each of the arms of the support is released and the driver turns off drive of the support.

3. The medical holding apparatus according to claim 1, wherein the processor is configured to calculate the torque by Equation of $T_{TTL}=T_{zoom}+T_{WD}-T_v$, where $T_{TTL}$ represents the torque, $T_{zoom}$ represents a parameter calculated from the enlargement factor, $T_{WD}$ represents a parameter calculated from the working distance, and $T_v$ represents a parameter calculated from the moving speed.

4. The medical holding apparatus according to claim 1, wherein the load applier is arranged in each of two or more of the joints, and the processor is configured to set the torque independently for each of the joints.

5. The medical holding apparatus according to claim 1, wherein the processor is configured to set the torque by using the enlargement factor, the working distance, and the moving speed, and a coefficient corresponding to displacement in a moving direction of the imager.

6. The medical holding apparatus according to claim 1, wherein each of the joints includes:
   a fixing structure fixed to one of the two arms connected to each other; and
   a movable structure fixed to an other one of the two arms, the movable structure being rotatable relative to the fixing structure, and the load applier applies a resistance load against the rotation to the movable structure when the movable structure rotates relative to the fixing structure.

7. The medical holding apparatus according to claim 1, wherein the load applier includes a magnetic fluid device.

8. The medical holding apparatus according to claim 1, further comprising:
   a brake to inhibit rotation of each of the arms of the support.

9. A medical observation system comprising:
   an imager to capture an image of an observation object in an enlarged manner and output an image signal corresponding to the image;
   a support including:
      a plurality of arms; and
      a plurality of joints to connect the plurality of arms, the support being configured to support the imager at a distal end thereof;
   a load applier arranged in at least one of the joints to apply a resistance load against operation of the at least one of the joints to the support; and
   a processor comprising hardware, the processor being configured to:
      set torque to be applied by the load applier based on an operating state of the imager; and
      apply a load corresponding to the set torque to the load applier when a rotation inhibit state of each of the arms of the support is released,
   wherein the processor is configured to set the torque based on an enlargement factor, a working distance, and a moving speed of the imager.

* * * * *